(12) United States Patent
Sasaki et al.

(10) Patent No.: US 8,227,234 B2
(45) Date of Patent: Jul. 24, 2012

(54) PROCESS FOR PREPARING 2-HYDROXY-4-SUBSTITUTED PYRIDINES

(75) Inventors: Mie Sasaki, Tokyo (JP); Seiichiro Matsumoto, Tokyo (JP)

(73) Assignee: Yuki Gosei Kogyo Co., Ltd., Tokyo (JP)

( * ) Notice: Subject to any disclaimer, the term of this patent is extended or adjusted under 35 U.S.C. 154(b) by 177 days.

(21) Appl. No.: 12/854,261

(22) Filed: Aug. 11, 2010

(65) Prior Publication Data

US 2011/0027864 A1 Feb. 3, 2011

Related U.S. Application Data

(62) Division of application No. 11/575,455, filed as application No. PCT/JP2005/017175 on Sep. 16, 2005, now Pat. No. 7,803,585.

(30) Foreign Application Priority Data

Sep. 17, 2004 (JP) .................................. 2004-270800

(51) Int. Cl.
*C12N 1/12* (2006.01)
(52) U.S. Cl. .................................................... 435/252.1
(58) Field of Classification Search ................ 435/252.1
See application file for complete search history.

(56) References Cited

U.S. PATENT DOCUMENTS 4,968,803 A 11/1990 Van Der Puy

FOREIGN PATENT DOCUMENTS

JP 01-193247 3/1989

OTHER PUBLICATIONS

European Search Report dated Jun. 16, 2009 for European Patent Application No. 05783619.9.
Gupta, R.C. et al. "Metabolism of Isonazid and Related Compounds by Microorganisms: Isolation, Characterization & Growth of Isoniazid-Degrading Organism". Indian J of Experimental Biology, vol. 16, 1978, pp. 1047-1051.
Schlieper, et al., New Methods for the Synthesis of Base Sensitive Cyanopyrimidine and Cyanopyridine Nucleosides, Nucleosides & Nucleosides, 3(4), pp. 369-388, 1984.
Gupta, et al., 2-Hyrdoxy-Isonicotinic Acid-An Intermediate in Metabolism of Isonicotinic Acid Hydrazide & Isoicotinic Acid by Sarcina, Indian J. Biochem. Biophys., vol. 15, pp. 492-493 (1978).
Kretzer et al., A New Pathway for Isoicotinate Degradation by Mycobacterium sp. INA1, Journal of General Microbiology, 137, pp. 1073 to 1080 (1991).
Rozen et al., Novel Oxgenation of Pyridine and Quinoline Rings Using Acetyl Hypoflourite, Journal of American Chemical Society, 109, pp. 3789-3790 (1987).
Van Der Puy, Controlled, Regiospecific Oxidation of Pyridine Carboxylic Acids and Esters with Elemental Fluorine, Tetrahedron Letters, 29(35), pp. 4389 to 4392 (1988).
International Search Report for WO 2006/030909.

*Primary Examiner* — Herbert J Lilling
(74) *Attorney, Agent, or Firm* — Heslin Rothenberg Farley & Mesiti P.C.

(57) ABSTRACT

A process for preparing a 2-hydroxy-4-substituted pyridine compound using a microbiological method, a novel microorganism, and a novel compound are provided.

1 Claim, No Drawings

SEQUENCE LISTING

<160> NUMBER OF SEQ ID NOS: 3

<210> SEQ ID NO 1
<211> LENGTH: 520
<212> TYPE: DNA
<213> ORGANISM: Delftia sp.

<400> SEQUENCE: 1

```
tggagagttt gatcctggct cagattgaac gctggcggca tgccttacac atgcaagtcg      60
aacggtaaca ggtcttcgga cgctgacgag tggcgaacgg gtgagtaata catcggaacg     120
tgcccagtcg tgggggataa ctactcgaaa gagtagctaa taccgcatac gatctgagga     180
tgaaagcggg ggaccttcgg gcctcgcgcg attggagcgg ccgatggcag attaggtagt     240
tggtgggata aaagcttacc aagccgacga tctgtagctg gtctgagagg acgaccagcc     300
acactgggac tgagacacgg cccagactcc tacgggaggc agcagtgggg aattttggac     360
aatgggcgaa agcctgatcc agcaatgccg cgtgcaggat gaaggccttc gggttgtaaa     420
ctgcttttgt acggaacgaa aaagcttctc ctaatacgag aggcccatga cggtaccgta     480
agaataagca ccggctaact acgtgccagc agccgcggta                           520
```

<210> SEQ ID NO 2

```
<211> LENGTH: 520
<212> TYPE: DNA
<213> ORGANISM: Delftia sp.

<400> SEQUENCE: 2
tggagagttt gatcctggct cagattgaac gctggcggca tgccttacac atgcaagtcg      60
aacggtaaca ggtcttcgga cgctgacgag tggcgaacgg gtgagtaata catcggaacg     120
tgcccagtcg tgggggataa ctactcgaaa gagtagctaa taccgcatac ratctgagga     180
tgaaagcggg ggaccttcgg gcctcgcgcg attggagcgg ccgatggcag attaggtagt     240
tggtgggata aaagcttacc aagccgacga tctgtagctg gtctgagagg acgaccagcc     300
acactgggac tgagacacgg cccagactcc tacgggaggc agcagtgggg aattttggac     360
aatgggcgaa agcctgatcc agcaatgccg cgtgcaggat gaaggccttc gggttgtaaa     420
ctgcttttgt acggaacgaa aaagctcctt ctaatacagg gggcccatga cggtaccgta     480
agaataagca ccggctaact acgtgccagc agccgcggta                          520

<210> SEQ ID NO 3
<211> LENGTH: 520
<212> TYPE: DNA
<213> ORGANISM: Acidovorax sp.

<400> SEQUENCE: 3
tggagagttt gatcctggct cagattgaac gctggcggca tgccttacac atgcaagtcg      60
aacggtaaca ggtcttcgga tgctgacgag tggcgaacgg gtgagtaata catcggaacg     120
tgcccgatcg tgggggataa cggagcgaaa gctttgctaa taccgcatac gatctacgga     180
tgaaagcagg ggaccgcaag gccttgcgcg gacggagcgg ccgatggcag attaggtagt     240
tggtgggata aaagcttacc aagccgacga tctgtagctg gtctgagagg acgaccagcc     300
acactgggac tgagacacgg cccagactcc tacgggaggc agcagtgggg aattttggac     360
aatgggcgaa agcctgatcc agccatgccg cgtgcaggat gaaggccttc gggttgtaaa     420
ctgcttttgt acggaacgaa aagactcctt ctaataaagg gggtccatga cggtaccgta     480
agaataagca ccggctaact acgtgccagc agccgcggta                          520
```

PROCESS FOR PREPARING 2-HYDROXY-4-SUBSTITUTED PYRIDINES

CROSS REFERENCE TO RELATED APPLICATIONS

This application is a divisional application of U.S. patent application Ser. No. 11/575,455, allowed, which is a 35 U.S.C. §371 U.S. national stage filing from PCT Application Ser. No. PCT/JP2005/017175, having an international filing date of Sep. 16, 2005, published in Japanese on Mar. 23, 2006 under Publication No. WO2006/030909, which claims priority from Application Ser. No. 2004-270800, filed Sep. 17, 2004. All prior applications listed are hereby incorporated by reference in their entirety.

REFERENCE TO A SEQUENCE LISTING

This application contains a sequence listing, provided as a paper copy, as required under 37 C.F.R. §1.821 (c), and is herein incorporated by reference in its entirety, as required under 37 C.F.R. §1.52 (e) (5). A copy of the sequence listing is also provided under 37 C.F.R. §1.821 (e), as a computer readable form.

TECHNICAL FIELD

The present invention relates to a process for preparing a 2-hydroxy-4-substituted pyridine wherein a microorganism is used to convert a 4-substituted pyridine to a corresponding 2-hydroxy-4-substituted pyridine. The 2-hydroxy-4-substituted pyridine is used as an intermediate of various fine chemicals as well as an intermediate of medicines and agricultural chemicals, and is a useful compound industrially.

BACKGROUND ART

Several processes for the preparation of the 2-hydroxy-4-substituted pyridine compounds by chemical synthesis are reported. For example, as a process for the preparation of a 2-hydroxyisonicotinic acid or a precursor thereof, that is, 2-halogenoisonicotinic acid, a process whereby
[i] isonicotinic acid is reacted with fluorine gas at ice-bath temperature, and thereafter the reactant is hydrolyzed with hydrochloric acid to obtain a 2-hydroxyisonicotinic acid (U.S. Pat. No. 4,968,803: Patent Reference 1), or
[ii] isonicotinic acid N-oxide is reacted with phosphorus oxychloride and phosphorus pentachroride under refluxing to obtain a 2-chloroisonicotinic acid (Japanese Examined Patent Publication (Kokoku) 6-37472: Patent Reference 2), is known.

As a process for the preparation of a 2-hydroxy-4-cyanopyridine, a process whereby
[iii]-4-cyanopyridine N-oxide is reacted with trifluoroacetic anhydride for 7 days at 110° C. to obtain a 4-cyano-2-pyridone [Nucleosides & Nucleotides, 3(4), 369-388, (1984): Non-Patent Reference 1] is reported.

As a process for the preparation of 2-hydroxy-4-methylpyridine, a process whereby [iv]-4-methylpyridine is reacted with acetyl hypofluorite at −10° C. to obtain a 2-acetoxy-4-methylpyridine, and thereafter the 2-acetoxy-4-methylpyridine is hydrolyzed to obtain 4-methyl-2-pyridone is reported [Journal of the American Chemical Society, 109, 3789-3790, (1987): Non-Patent Reference 2].

A process for the preparation of a 2-hydroxyisonicotinamide is not known. In addition, 2-hydroxy-4-pyridinaldoxime, which is not described in any reference, is a novel compound.

However, among these preparing processes [i] to [iv], in the process [i] a careful handling of halogen gas is required, and further, a special apparatus is required in the reaction. In addition, the processes [ii] to [iv] are not considered as an industrial process, due to a use of particular reagents, a strict temperature conditions, and many complicated steps. Accordingly, these processes by chemical synthesis are not practical processes because the processes have many steps and materials requiring careful handling are used.

A process for the preparation of a 2-hydroxy-4 substituted pyridine by using a microbiological method has not been reported until now. As a microorganism which has an enzymatic activity capable of converting an isonicotinic acid into a 2-hydroxyisonicotinic acid, *Sarcina* species [Indian Journal of Biochemistry & Biophysics, 15, December, 492-493, (1978): Non-Patent Reference 3] and Mycobacterium species [Journal of General Microbiology, 137, 1073-1080, (1991): Non-Patent Reference 4] are known. However, the Non-Patent Reference 3 and Non-Patent Reference 4 are disclosed only an analysis of a metabolic pathway of the microorganisms and do not disclose the process of preparing the 2-hydroxyisonicotinic acid, which is a metabolic intermediate. Therefore, taking a capacity of enzyme production of the microorganisms and an amount of the 2-hydroxyisonicotinic acid accumulated into consideration, the process using the microorganisms can not be satisfactorily used in an industrial production of the 2-hydroxyisonicotinic acid.

[Patent Reference 1] U.S. Pat. No. 4,968,803

[Patent Reference 2] Japanese Examined Patent Publication (Kokoku) 6-37472

[Non-Patent Reference 1] Nucleosides & Nucleotides, 3(4), 369-388, (1984)

[Non-Patent Reference 2] Journal of the American Chemical Society, 109, 3789-3790, (1987)

[Non-Patent Reference 3] Indian Journal of Biochemistry & Biophysics, 15, December, 492-493, (1978)

[Non-Patent Reference 4] Journal of General Microbiology, 137, 1073-1080, (1991)

DISCLOSURE OF THE INVENTION

Problems to be Solved by the Invention

The present inventors have conducted intensive studies in an attempt to establish a process which can be used industrially, and found the presence of microorganisms capable of preparing a corresponding 2-hydroxy-4-substituted pyridine from a 4-substituted pyridine in a significant amount, and accumulating the same. Therefore, the inventors found that a process, which is usable industrially, for preparing the corresponding 2-hydroxy-4-substituted pyridine from the 4-substituted pyridine by using the microorganism is provided.

The present invention is based on the above findings.

Means for Solving the Problems

Accordingly, the present invention relates to a process for preparing a 2-hydroxy-4-substituted pyridine of the general formula (2):

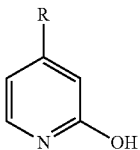

(2)

wherein R is a methyl group, a carboxyl group, a carbamoyl group, a hydroxyiminomethyl group or a cyano group, characterized in that a function of a microorganism or a product obtained therefrom, is exerted on a 4-substituted pyridine of the general formula (1):

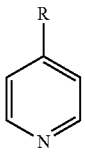

(1)

wherein R is a methyl group, a carboxyl group, a carbamoyl group, a hydroxyiminomethyl group or a cyano group, the microorganism or product obtained therefrom being capable of introducing a hydroxyl group to the 2-position of the 4-substituted pyridine.

According to a preferable embodiment of the present invention, the microorganism belongs to the *Delftia* genus or *Acidovorax* genus.

According to a more preferable embodiment of the present invention, the microorganism is the *Delftia* species YGK-A649 (FERM BP-10389), *Delftia* species YGK-C217 (FERM BP-10388), or *Acidovorax* species YGK-A854 (FERM BP-10387).

The present invention also relates to a microorganism selected from a group consisting of the *Delftia* species YGK-A649 (FERM BP-10389), *Delftia* species YGK-C217 (FERM BP-10388), and *Acidovorax* species YGK-A854 (FERM BP-10387).

Further, the present invention relates to a 2-hydroxy-4-pyridinaldoxime, which is a novel compound, of the formula (3):

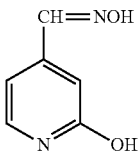

(3)

Effects of the Invention

According to the process of present invention, the corresponding 2-hydroxy-4-substituted pyridine can be prepared from the 4-substituted pyridine safety at a single step, under a condition of an ordinary temperature and ordinary pressure, and the process for preparation is also usable industrially.

BRIEF DESCRIPTION OF THE DRAWINGS

The 4-substituted pyridine of the general formula (1) used as a starting material in the process of the present invention, may include 4-methylpyridine (alias: γ-picoline: R=methyl group), isonicotinic acid (R=carboxyl group), isonicotinamide (R=carbamoyl group), 4-pyridinaldoxime (R=hydroxyiminomethyl group) and 4-cyanopyridine (R=cyano group).

When an isonicotinic acid is used as the starting material, isonicotinic acid or a salt thereof may be used. As the salt of isonicotinic acid, there may be mentioned, for example, alkali metal salt such as sodium salt and potassium salt, alkaline earth metal such as magnesium salt and calcium salt, or ammonium salt.

As the 4-substituted pyridine used as the starting material in the process of the present invention, the 4-substituted pyridine per se may be used, and a reaction solution per se obtained by a synthesis of the 4-substituted pyridine may be also used. When a 4-pyridinaldoxime is used as the starting material, for example, the 4-pyridinaldoxime per se may be used and a reaction solution per se containing 4-pyridinaldoxime, which is synthesized from 4-pyridinecarbaldehyde, may be also used.

An origin of the microorganism used in the process of the present invention is not limited, so long as it can be used to prepare the corresponding 2-hydroxy-4-substituted pyridine of the general formula (2) from the 4-substituted pyridine of the general formula (1) in a significant amount, and accumulate the same.

As the microorganism capable of preparing the corresponding 2-hydroxy-4-substituted pyridine of the general formula (2) from 4-substituted pyridine of the general formula (1) in a significant amount, and accumulating the same, a microorganism belonging to the *Delftia* genus or *Acidovorax* genus is preferable.

Further, a preferable embodiment of the microorganism, in particular, includes the *Delftia* species YGK-A649 (FERM BP-10389), *Delftia* species YGK-C217 (FERM BP-10388), or *Acidovorax* species YGK-A854 (FERM BP-10387). The *Delftia* species YGK-A649 was originally deposited on Jul. 27, 2004, and the *Delftia* species YGK-C217, and *Acidovorax* species YGK-A854(FERM BP-10387) were originally deposited on Mar. 18, 2004, in the International Patent Organism Depositary National Institute of Advanced Industrial Science and Technology (Address: Tsukuba Central 6, 1-1, Higashi 1-chome Tukuba-shi, Ibaraki-ken 305-8566 Japan), and were transferred from the original deposit to an international deposit on Aug. 2, 2005. International deposit number (the number in the bracket ([ ]) followed by the international deposit number is the original deposit number) was FERM BP-10389 [FERM P-20138], FERM BP-10388 [FERM P-19740], FERM BP-10387 [FERM P-19741], respectively.

The bacterial properties of the *Delftia* species YGK-A649 strain (international deposit number FERM BP-10389 [original deposit number FERM P-20138]) which can be used in the process according to the present invention are as follows:
1. Morphological properties and culturing properties
(1) Cell morphology: rod-shaped bacteria
(2) Width: 0.8 μm
(3) Length: 1.5-2.0 μm
(4) Spore formation: negative
(5) Motility: positive
(6) Colony morphology: peripheral border, entire margin; swelling, lenticular; surface shape, smooth; cream color
2. Physiological Properties
(1) Gram's stain: negative
(2) Growth at 37° C. and 45° C.: 37° C. positive, 45° C. negative
(3) Catalase: positive
(4) Oxidase: positive (5) Acid/gas production (glucose): negative/negative
(6) O/F test (glucose): negative/negative
(7) Reduction of a nitrate: positive
(8) Production of indole: negative
(9) Glucose acidification: negative
(10) Arginine dihydrolase: negative
(11) Urease: negative
(12) Hydrolysis of esculin: negative
(13) Hydrolysis of gelatin: negative
(14) β-galactosidase: negative
(15) Utilization of several compounds
　　Glucose: negative
　　L-arabinose: negative
　　D-mannose: negative
　　D-mannitol: positive
　　N-acetyl-D-glucosamine: negative
　　Maltose: negative
　　Potassium gluconate: positive
　　n-capric acid: positive
　　Adipic acid: positive
　　dl-malic acid: positive
　　Sodium citrate: negative
　　Phenyl acetate: positive
(16) Cytochrome oxidase: positive
(17) Growth in MacConkey agar: positive 3. Chemical taxonomic properties A genomic DNA was extracted from the present bacteria strain and a nucleotide sequence of about 500 bases of 5' end in 16S rRNA gene (16S rDNA) was analyzed. The determined base sequence is shown in SEQ ID NO: 1 of SEQUENCE LISTING. The homology of the resulting base sequence of 16s rDNA of the present bacteria strain (SEQ ID NO: 1) against base sequences in DNA sequence databases (GenBank/DDBJ/EMBL) was searched, and the phylogenetic tree between the present bacteria and related bacteria provided. From the result, it was considered that the present bacteria belong to the *Delftia* genus. The most relative type strain is the *Delftia acidovorans* IAM12409 strain [Accession No. AB021417], and a sequence homology between the present bacteria and the *Delftia acidovorans* IAM12409 strain is 99%.

The present bacteria strain was determined as the *Delftia* species from the above result. Accordingly, the present invention also relates to the novel bacteria strain.

The bacterial properties of the *Delftia* species YGK-C217 (international deposit number FERM BP-10388 [original deposit number FERM P-19740]) strain which can be used in the process according to the present invention are as follows:

1. Morphological properties and culturing properties
(1) Cell morphology: rod-shaped bacteria
(2) Width: 0.8 μm
(3) Length: 1.5-3.0 μm
(4) Spore formation: negative
(5) Motility: positive
(6) Colony morphology: peripheral border, slightly wave shaped; low convexity; glossy; cream color 2. Physiological Properties
(1) Gram's stain: negative
(2) Growth at 37° C. and 45° C.: 37° C. positive, 45° C. negative
(3) Catalase: positive
(4) Oxidase: positive
(5) Acid/gas production (glucose): negative/negative
(6) O/F test (glucose): negative/negative (alkalis productive)
(7) Reduction of a nitrate: positive
(8) Production of indole: negative
(9) Glucose acidification: negative
(10) Arginine dihydrolase: negative
(11) Urease: negative
(12) Hydrolysis of esculin: negative
(13) Hydrolysis of gelatin: negative
(14) β-galactosidase: negative
(15) Utilization of several compounds
　　Glucose: negative
　　L-arabinose: negative
　　D-mannose: negative
　　D-mannitol: positive
　　N-acetyl-D-glucosamine: negative
　　Maltose: negative
　　Potassium gluconate: positive
　　n-capric acid: positive
　　Adipic acid: positive
　　dl-malic acid: positive
　　Sodium citrate: negative
　　Phenyl acetate: positive
(16) Cytochrome oxidase: positive 3. Chemical taxonomic properties A genomic DNA was extracted from the present bacteria strain and a nucleotide sequence of about 500 bases of 5' end in 16S rRNA gene (16S rDNA) was analyzed. The determined base sequence is shown in SEQ ID NO: 2 of SEQUENCE LISTING. The homology of the resulting base sequence of 16s rDNA of the present bacteria strain (SEQ ID NO: 2) against base sequences in DNA sequence databases (GenBank/DDBJ/EMBL) was searched, and the phylogenetic tree between the present bacteria and related bacteria provided. From the result, it was considered that the present bacteria belong to the *Delftia* genus. The most relative type strain is the *Delftia tsuruhatensis* T7 strain [Accession No. AB075017], and a sequence homology between the present bacteria and the *Delftia tsuruhatensis* T7 strain is 99%.

The present bacteria strain was determined as the *Delftia* species from the above result. Accordingly, the present invention also relates to the novel bacteria strain.

The bacterial properties of the *Acidovorax* species YGK-A854 (international deposit number FERM BP-10387 [original deposit number FERM P-19741]) strain which can be used in the process according to the present invention are as follows:

1. Morphological properties and culturing properties
(1) Cell morphology: rod-shaped bacteria
(2) Width: 0.7-0.8 μm
(3) Length: 1.5-2.0 μm
(4) Spore formation: negative
(5) Motility: positive
(6) Colony morphology: peripheral border, smooth; low convexity; glossy; cream color 2. Physiological Properties
(1) Gram's stain: negative
(2) Growth at 37° C. and 45° C.: 37° C. positive, 45° C. negative
(3) Catalase: positive
(4) Oxidase: positive
(5) Acid/gas production (glucose): negative/negative
(6) O/F test (glucose): negative/negative
(7) Reduction of a nitrate: positive
(8) Production of indole: negative
(9) Glucose acidification: negative
(10) Arginine dihydrolase: negative
(11) Urease: negative
(12) Hydrolysis of esculin: negative
(13) Hydrolysis of gelatin: negative
(14) β-galactosidase: negative
(15) Utilization of several compounds Glucose: positive
L-arabinose: negative
D-mannose: negative
D-mannitol: negative
N-acetyl-D-glucosamine: negative
Maltose: negative
Potassium gluconate: positive
n-capric acid: negative
Adipic acid: negative
dl-malic acid: negative
Sodium citrate: negative
Phenyl acetate: negative
(16) Cytochrome oxidase: positive
(17) Hydrolysis of Tween 80: positive 3. Chemical taxonomic properties A genomic DNA was extracted from the present bacteria strain and a nucleotide sequence of about 500 bases of 5' end in 16S rRNA gene (16S rDNA) was analyzed. The determined base sequence is shown in SEQ ID NO: 3 of SEQUENCE LISTING. The homology of the resulting base sequence of 16s rDNA of the present bacteria strain (SEQ ID NO: 3) against base sequences in DNA sequence databases (GenBank/DDBJ/EMBL) was searched, and the phylogenetic tree between the present bacteria and related bacteria provided. From the result, it was considered that the present bacteria belong to the *Acidovorax* genus. The most relative type strain is the *Acidovorax defluvii* BSB411 strain [Accession No. Y18616], and a sequence homology between the present bacteria and *Acidovorax defluvii* BSB411 strain is 99%.

The present bacteria strain was determined as the *Delftia* species from the above result. Accordingly, the present invention also relates to the novel bacteria strain.

Now, a culture method for the microorganism belonging to the *Delftia* genus or *Acidovorax* genus used in the process according to the present invention will be illustrated. In particular, the culture method for the *Delftia* species YGK-A649 (FERM BP-10389), *Delftia* species YGK-C217 (FERM BP-10388), or *Acidovorax* species YGK-A854 (FERM BP-10387), which is the novel microorganism according to the present invention, will be illustrated.

A medium for culturing the microorganisms is not particularly limited, so long as these microorganisms may be commonly grown therein, and thus, any common and known culture medium for microorganisms can be used. As a carbon source and a nitrogen source, for example, yeast extract, peptone, meat extract and/or amino acid may be used. Further, if necessary, organic acid, trace metal salt, vitamins, nucleic acid related substance, and/or inorganic salts, etc. can be added to the culture medium.

In addition, if necessary, the 4-substituted pyridine may be added to the culture medium and the culture can be carried out, in order to bring out the ability to prepare the corresponding 2-hydroxy-4-substituted pyridine of the general formula (2) from the 4-substituted pyridine of the general formula (1) at a maximum. In this case, a rate of the amount of the 4-substituted pyridine added to the culture medium is 0.01-3.0 w/v %, preferably 0.3-2.0 w/v %.

A temperature for culturing the microorganisms is preferably 10 to 37° C., more preferably 23 to 32° C. The pH of culture medium when culturing is preferably pH 6.0-10.0, more preferably pH 6.5-9.0. The culture is preferably carried out under an aerobic condition, and thus, an aeration and stirring are preferably carried out in the case of a liquid culture. A culture time in a batch culture is preferably 10 hours to 1 week, more preferably 1 to 3 days.

As mentioned above, the cultured bacterial cells of the microorganism, in particular the novel microorganisms according to the present invention can be accumulated in the culture medium. [i] The obtained culture per se may be used for the below-mentioned accumulating reaction, [ii] the recovered microorganism from the culture may be used for the accumulating reaction, and further [iii] the product obtained from recovered microorganism, such as a fractured product of the microorganism, crude enzyme, purified enzyme or the like, may be used for the accumulating reaction.

Subsequently, the accumulating reaction, wherein the microorganism (particularly the novel microorganisms according to the present invention) or the product obtained from the microorganism is used to prepare the corresponding 2-hydroxy-4-substituted pyridine of general formula (2) from the 4-substituted pyridine of general formula (1), is carried out. The accumulating reaction can be carried out batch-wise, or continuously by using a bioreactor and the like. When the accumulating reaction is carried out batch-wise, the culture time of several hours to 1 week is sufficient.

The above process [i] is illustrated as follows. Particularly, the accumulating reaction, in which the corresponding 2-hydroxy-4-substituted pyridine of general formula (2) is accumulated in the reaction system, can be started by adding the 4-substituted pyridine of general formula (1) directly to the culture containing the microorganism grown by the above culture method. The pH of the medium in the accumulating reaction is preferably pH 6.0-10.0, more preferably pH 6.0-9.0. A temperature in the accumulating reaction is preferably 10 to 40° C., more preferably 10 to 35° C. A rate of the amount of the 4-substituted pyridine added to the culture medium is 0.1-5.0 w/v %, preferably 0.5-3.0 w/v %. The 4-substituted pyridine may be added at one time. If an inhibition of the accumulating reaction due to a highly concentrated 4-substituted pyridine is found, however, the 4-substituted pyridine may be added little by little.

The accumulating reaction of the corresponding 2-hydroxy-4-substituted pyridine can be started from the time the microorganism is sufficiently grown and has obtained a sufficient ability to convert. However, even in the early stage of the culture, the 4-substituted pyridine of a concentration range, wherein a growth of the microorganism is not inhibited, may be added so that the culture of the microorganism and the accumulation reaction of the corresponding 2-hydroxy-4-substituted pyridine can be carried out simultaneously.

In the case of the above process [ii], the grown microorganism according to the above method is recovered from the culture by filtration or centrifugation, and can be used in the accumulating reaction. That is, the resulting microorganism is suspended in an aqueous solvent such as a normal saline solution or buffer solution, containing the 4-substituted pyridine, and can be used in the accumulating reaction. The conditions for the accumulating reaction (such as pH, temperature, amount of added 4-substituted pyridine) of this process [ii] are same as those of the process [i]. Further, in the case of the above process [iii], the product obtained from the recovered microorganism, such as fractured product of microorganism, crude enzyme, purified enzyme or the like, is suspended in an aqueous solvent such as a normal saline solution or buffer solution, containing the 4-substituted pyridine, and can be used in the accumulating reaction. The conditions for the accumulating reaction of this process [iii] are same as those of the process [i]. Alternatively, the microorganism or the product obtained therefrom is immobilized to an appropriate carrier by a known method, the immobilized product may be used in the accumulating reaction by being placed contact with the above-mentioned aqueous solvent.

As the aqueous solvent used in the accumulating reaction using the microorganism or the product obtained therefrom, there may be mentioned a normal saline solution, potassium phosphate buffer, tris-hydrochloric acid buffer, glycin-sodium hydrate buffer, boric acid-sodium hydrate buffer, or the like.

If necessary, the microorganism is removed by filtration or centrifugation from the resulting broth after the accumulating reaction as above. Thereafter, the 2-hydroxy-4-substituted pyridine is precipitated by adding the acid solution such as hydrochloric acid or sulfuric acid to the broth, whereby it may be recovered. When the product obtained from the microorganism such as the crude enzyme or the purified enzyme is used, the step for a removal of the bacterial cells can be omitted. In addition, the 2-hydroxy-4-substituted pyridine may also be recovered by a known purification method such as a chromatography technique.

Biological Deposits

*Acidovorax* sp. YGK-A854 has been deposited, in accordance with the Budapest Treaty, with the International Patent Organism Depositary, National Institute of Advanced Industrial Science and Technology, AIST Tsukuba Central 6, 1-1, Higashi 1-Chrome Tsukuba-shi, Ibaraki-ken 305-8566, Japan, on Mar. 18, 2004, under deposit number Number FERM BP-10387. *Delftia* sp. YGK-C217 has been deposited, in accordance with the Budapest Treaty, with the International Patent Organism Depositary, National Institute of Advanced Industrial Science and Technology, AIST Tsukuba Central 6, 1-1, Higashi 1-Chrome Tsukuba-shi, Ibaraki-ken 305-8566, Japan, on Mar. 18, 2004, under deposit number FERM BP-10388. *Delftia* sp. YGK-A649 has been deposited, in accordance with the Budapest Treaty, with the International Patent Organism Depositary, National Institute of Advanced Industrial Science and Technology, AIST Tsukuba Central 6, 1-1, Higashi 1-Chrome Tsukuba-shi, Ibaraki-ken 305-8566, Japan, on Jul. 27, 2004, under deposit number FERM BP-10389. International Patent Organism Depositary was established as one of the depositaries designated by the Commissioner of the Japanese Patent Office (JPO), and as one of the International Depositary Authorities (IDAs) of the Budapest Treaty organized by the World Intellectual Property Organization (WIPO). In accordance with United States Code of Federal Regulations (see CFR §1.808) and USPTO's Manual of Patent Examination Procedure §2410.01, all restrictions imposed by the depositor on the availability to the public of the deposited material will be irrevocably removed upon granting of the patent.

EXAMPLES

The present invention will now be further illustrated by, but is by no means limited to, the following Examples.

The media used in the Examples are described as follows.

(1) Medium A 1.25 g of yeast extract, 4.3 g of disodium hydrogenphosphate 12 hydrate, 4.2 g of potassium dihydrogen phosphate, 0.3 g of iron(II) sulfate 7 hydrate, 0.3 g of disodium molybdate(VI) 2 hydrate, 0.5 g of magnesium sulfate 7 hydrate, and 5.0 g of isonicotinic acid are added to 1.0 L of demineralized water and the solution is adjusted to pH 7.0 by a sodium hydroxide solution.

(2) Medium B 1.25 g of yeast extract, 4.3 g of disodium hydrogenphosphate 12 hydrate, 4.2 g of potassium dihydrogen phosphate, 0.3 g of iron(II) sulfate 7 hydrate, 0.3 g of disodium molybdate(VI) 2 hydrate, 0.5 g of magnesium sulfate 7 hydrate, 5.0 g of isonicotinic acid, and 5.0 g of monosodium glutamate are added to 1.0 L of demineralized water and the solution is adjusted to pH 7.0 by a sodium hydroxide solution.

(3) Medium C 1.25 g of yeast extract, 1.0 g of SEALIFE (artificial sea-water components, Marinetech Co. Ltd.), 4.3 g of disodium hydrogenphosphate 12 hydrate, 4.2 g of potassium dihydrogenphosphate, 3.0 mg of iron(II) sulfate 7 hydrate, 3.0 mg of disodium molybdate(VI) 2 hydrate, and 5.0 g of isonicotinic acid are added to 1.0 L of demineralized water and the solution is adjusted to pH 7.0 or pH 9.0 by a sodium hydroxide solution. The pH of the medium after sterilization by an autoclave is pH 7.0 or pH 8.5, respectively.

Example 1

The Accumulating Reaction of 2-Hydroxy Isonicotinic Acid Using *Delftia* Species YGK-A649 in a Broth One hundred mL of the medium A was charged into a conical flask (500 mL volume) and was sterilized by an autoclave at 121° C., for 20 minutes. A piece of the bacteria of the *Delftia* species YGK-A649 (FERM BP-10389), which was picked up by a platinum loop from a nutrient agar wherein it was maintained, was inoculated to the medium in the conical flask and the whole was incubated at 27° C., for 24 hours while shaking.

Then 1 L of the medium B was charged into a jar fermenter (2 L volume) capable of shaking, aerating, controlling temperature, and controlling pH, and was sterilized by an autoclave at 121° C., for 20 minutes. Then, 10 mL of the above medium A solution cultured for 24 hours was added to the medium B in the jar fermenter, and the whole was cultured at 27° C., pH7.0, for 22 hours while shaking and aerating.

Thereafter, the broth was adjusted to pH 6.7 and an isonicotinic acid was added to the broth appropriately and intermittently so that the concentration range of the isonicotinic acid is maintained at 0.5-1.0 w/v %, whereby the accumulating reaction of the 2-hydroxyisonicotinic acid was carried out. The accumulation of the 2-hydroxyisonicotinic acid had not progressed at 77 hours later. At that time, the accumulating reaction was stopped. Then, a supernatant of the broth obtained by centrifugation was analyzed by HPLC under the following condition. An amount of the 2-hydroxyisonicotinic acid accumulated was 91.6 g (0.66 mol). A molar conversion rate of 2-hydroxyisonicotinic acid with respect to a sum 126.1 g (1.02 mol) of the isonicotinic acid contained in the medium A and the medium B, and isonicotinic acid added in broth of the accumulating reaction was 64.3%.

The bacterial cells were removed by centrifugation from the resulting broth containing 91.6 g (as a quantitative value) of the 2-hydroxyisonicotinic acid. Then, the 2-hydroxyisonicotinic acid was precipitated by hydrochloric acid and impurities were removed by a treatment using an activated charcoal to obtain white crystals. The dry weight of the resulting crystals was 81.5 g and an area rate by HPLC analysis was 100%. The resulting compound was identified as the 2-hydroxyisonicotinic acid by HPLC-MS, NMR and IR analysis.

[Conditions of HPLC Analysis]

Column; Develosil RPAQUEOUS 4.6×250 mm,
Mobile phase; 0.5 v/v % methanol (adjusted to pH 2.5 by adding 85% phosphoric acid),
Flow rate; 1 mL/min,
Temperature of column; 25° C.,
Detective wavelength; 210 nm, Retention time; isonicotinic acid=4.1 min, 2-hydroxyisonicotinic acid=16.9 min, 2,6-dihydroxyisonicotinic acid (alias: citrazinic acid)=18.6 min Example 2

Activity of Preparing 2-Hydroxyisonicotinic Acid of Isolated Bacteria Strains

Ten mL of medium C was charged into a test tube (25 mL volume), and was sterilized by an autoclave at 121° C., for 20 minutes. A piece of the bacteria of the *Delftia* species YGK-A649 (FERM BP-10389), *Delftia* species YGK-C217 (FERM BP-10388), or *Acidovorax* species YGK-A854 (FERM BP-10387), which was picked up by a platinum loop from a nutrient agar wherein it was maintained, was inoculated to the medium in the test tube respectively and the whole was incubated at 27° C., for 25 hours while shaking respectively. The medium C for the *Delftia* species YGK-A649 was adjusted to pH 7.0 after sterilization, and those for other species was adjusted to pH8.5.

After the culture was completed, the desired 2-hydroxyisonicotinic acid and 2,6-dihydroxyisonicotinic acid, which is a by-product, which are contained in the supernatant obtained by centrifugation from broth, were measured, and the molar rate (%) of 2-hydroxyisonicotinic acid converted from isonicotinic acid contained in the broth was calculated. The purity [P] of the 2-hydroxyisonicotinic acid was calculated from the following equation:

$$P=[a/(a+b)]\times 100$$

wherein "a" is a molar amount of the 2-hydroxyisonicotinic acid, "b" is a molar amount of the 2,6-dihydroxyisonicotinic acid.

In addition, the bacterial cells in 1 mL of the culture were collected by centrifugation, and the resulting bacterial cells were suspended in 0.5 mL of a 0.1 M potassium phosphate buffer (adjusted to pH 7.0) containing isonicotinic acid (0.5 w/v %). The suspension was incubated at 30° C., for 30 minute, while shaking. The amount of resulting 2-hydroxyisonicotinic acid and the amount of resulting 2,6-dihydroxyisonicotinic acid were determined by HPLC analysis. An accumulating reaction activity of the 2-hydroxyisonicotinic acid with respect to 1 L of broth (U/L broth) [hereinafter referred to as an activity of resting bacterial cell (U/L broth)] was determined under the condition that an amount (1 μmol/min) of 2-hydroxyisonicotinic acid accumulated was 1 unit (U). Then, according to the above equation, the purity of 2-hydroxyisonicotinic acid in a reaction of resting bacterial cell was calculated. The results are shown in Table 1. The title "2HINA" in the Table 1 denotes 2-hydroxyisonicotinic acid.

Example 3

Accumulating Reaction of the 2-Hydroxy-4-Substituted Pyridine Using a Resting Bacterial Cell of *Delftia* Species YGK-A649

As in Example 1, the *Delftia* species YGK-A649 (FERM BP-10389) was cultured, and thus, the bacterial cells in 200 mL of the culture were collected by centrifugation to obtain the resting bacterial cell. The resting bacterial cells were added to 100 mL of a 0.1 M potassium phosphate buffer (adjusted to pH 7.0) containing 4-substituted pyridine described in Table 2 (0.5 w/v %) respectively, and were suspended. The suspension was charged to a reaction vessel (100 mL volume) capable of shaking, aerating, controlling temperature, and controlling pH, and a reaction was carried out at 27° C., and pH 7.0, while shaking and aerating.

After the reaction for 44 hours, the 2-hydroxy-4-substituted pyridine was measured. The reaction products were identified by HPLC analysis and HPLC-MS. The results are shown in Table 2.

TABLE 2

| Substrate | Reaction time (hr) | Yield of products (g/L) | Molar conversion rate (%) |
|---|---|---|---|
| 4-cyanopyridine | 44 | 2.4 | 47 |
| 4-pyridinaldoxime | 44 | 5.0 | 100 |
| γ-picoline | 44 | 0.6 | 12 |

One hundred mL of isopropanol was added to the resulting broth containing 0.27 g of 2-hydroxy-4-pyridinaldoxime obtained from the reaction with 4-pyridinaldoxime as a substance. After shaking for 30 minutes, the solid contents were removed by filtration. After an addition of 100 mL of water to the filtrate, the whole was concentrated under a reduced pressure, whereby isopropanol was removed to precipitate the crystals. The precipitated crystals were separated by filtration to obtain 0.20 g of crude crystals. The resulting crystals were washed by water, and then were separated by filtration to obtain 0.15 g of white crystals of 2-hydroxy-4-pyridinaldoxime (rate of isolated yield=53%). The structure of the crystals was identified by IR analysis, proton NMR analysis and MS analysis.

IR(KBr, cm$^{-1}$); 3180, 3070, 2920, 1660, 1520, 1430, 1330, 1300, 1250, 1000, 900, 870, 800, 770

$^1$H-NMR (Dimethylsulfoxide, ppm); 11.78 (1H, s), 11.48 (1H, s), 7.95 (1H, s), 7.29 (1H, d), 6.40 (1H, s), 6.40 (1H, d)

MS (MH$^+$); 139

TABLE 1

| Bacteria strain | Accumulation of 2HINA in broth | | Accumulation of 2HINA in reaction of resting bacterial cell | |
|---|---|---|---|---|
| | Molar conversion rate (%) | Purity (%) | Activity of resting bacterial cell (U/L broth) | Purity (%) |
| *Delftia* sp. YGK-A649 | 14 | 99 | 86 | 100 |
| *Delftia* sp. YGK-C217 | 12 | 69 | 98 | 99 |
| *Acidovorax* sp. YGK-A854 | 5 | 48 | 3 | 73 |

Example 4

Accumulating Reaction of the 2-Hydroxy-4-Substituted Pyridine Using a Resting Bacterial Cell of Each Bacteria As in Example 1, the *Delftia* species YGK-A649 (FERM BP-10389), *Delftia* species YGK-C217(FERM BP-10388), or *Acidovorax* species YGK-A854(FERM BP-10387) was cultured, and then each bacteria in 10 mL of the culture was collected by centrifugation to obtain the resting bacterial cells. Then each resting bacterial cells were added to 2 mL of a 0.1 M boric acid-sodium hydrate buffer (adjusted to pH7.0) containing 4-substituted pyridine described in Table 3 (0.5 w/v %) respectively, and were suspended. Then each suspension was charged to a reaction vessel (15 mL volume) and a reaction was carried out at 27° C., pH7.0, while shaking. After the reaction for 44 hours, each 2-hydroxy-4-substituted pyridine was measured. The results are shown in Table 3.

TABLE 3

| Substrate | Molar conversion rate of each bacteria strain in reaction of resting bacterial cell (%) | | |
|---|---|---|---|
| | YGK-A649 | YGK-C217 | YGK-A854 |
| isonicotinamide | 46 | 38 | 56 |
| 4-cyanopyridine | 18 | 0 | 19 |
| 4-pyridinaldoxime | 42 | 80 | 100 |
| γ-picoline | 10 | 10 | 4 |

Example 5

Accumulating Reaction of the 2-Hydroxy-4-Pyridinaldoxime Using a Resting Bacterial Cell of *Delftia* Species YGK-A649

1.3 g of hydroxylamine hydrochloride was solved to 5 g of ion-exchange water, and the solution was heated to 65° C. Then 2 g of 4-pyridinecarbaldehyde was added dropwise. The reaction was carried out at 65° C., for 30 minutes, and a solution containing 2.2 g of 4-pyridinaldoxime was obtained. The resulting 4-pyridinaldoxime was identified by HPLC analysis. Thereafter, the reaction solution was cooled to 30° C., and was neutralized by saturated sodium hydrogen carbonate solution to be adjusted to pH 6. Six hundred mL of 0.1M potassium phosphate buffer (adjusted to pH 7.0) was added to the neutralized solution. Further, as in Example 1, the *Delftia* species YGK-A649 (FERM BP-10389) was cultured, and thus, the bacterial cells in 1000 mL of the culture was collected by centrifugation to obtain the resting bacterial cells and then form a suspension thereof. The suspension was charged to a reaction vessel (2000 mL volume) capable of shaking, aerating, controlling temperature, and controlling pH, and a reaction was carried out at 20° C., and pH 7-8, while shaking and aerating. After the reaction for 108 hours, 2-hydroxy-4-pyridinaldoxime was obtained at yield rate of 87% in the reaction. The analysis values of the resulting 2-hydroxy-4-pyridinaldoxime by IR analysis, proton NMR analysis and MS analysis were the same as the values described in Example 3, and thus, the structure of the resulting 2-hydroxy-4-pyridinaldoxime was identified.

INDUSTRIAL APPLICABILITY

According to the process of the present invention, a microorganism can be used to convert a 4-substituted pyridine to a corresponding 2-hydroxy-4-substituted pyridine. As the process for preparation is usable industrially, the 2-hydroxy-4-substituted pyridine, which is a useful compound as an intermediate of various fine chemicals as well as an intermediate of medicines and agricultural chemicals, can be provided.

Although the present invention has been described with reference to specific embodiments, various changes and modifications obvious to those skilled in the art are possible without departing from the scope of the appended claims.

The invention claimed is:

1. A microorganism selected from a group consisting of *Delftia* species YGK-A649 (FERM BP-10389), *Delftia* species YGK-C217(FERM BP-10388), and *Acidovorax* species YGK-A854(FERM BP-10387).

* * * * *